(12) United States Patent
O'Brien

(10) Patent No.: US 11,093,552 B2
(45) Date of Patent: Aug. 17, 2021

(54) UNBIASED DRUG SELECTION FOR AUDIT USING DISTRIBUTED LEDGER TECHNOLOGY

(71) Applicant: OMNY, Inc., Redwood City, CA (US)

(72) Inventor: Sean O'Brien, Atlanta, GA (US)

(73) Assignee: OMNY, Inc., Redwood City, CA (US)

( * ) Notice: Subject to any disclaimer, the term of this patent is extended or adjusted under 35 U.S.C. 154(b) by 391 days.

(21) Appl. No.: 16/385,730

(22) Filed: Apr. 16, 2019

(65) Prior Publication Data

US 2019/0317964 A1 Oct. 17, 2019

Related U.S. Application Data

(60) Provisional application No. 62/658,312, filed on Apr. 16, 2018.

(51) Int. Cl.
| | | |
|---|---|---|
| G06F 16/9035 | (2019.01) | |
| H04L 9/06 | (2006.01) | |
| G06F 17/18 | (2006.01) | |

(52) U.S. Cl.
CPC ......... *G06F 16/9035* (2019.01); *G06F 17/18* (2013.01); *H04L 9/0643* (2013.01); *H04L 2209/38* (2013.01)

(58) Field of Classification Search
CPC ... G06F 16/9035; G06F 17/18; H04L 9/0643; H04L 2209/38
USPC ......................................................... 707/748
See application file for complete search history.

(56) References Cited

U.S. PATENT DOCUMENTS

| 10,868,676 B2* | 12/2020 | Nguyen | H04L 9/0643 |
| 2017/0199987 A1* | 7/2017 | Loeb | G16H 50/70 |
| 2020/0065826 A1* | 2/2020 | Gering | G16H 20/10 |

OTHER PUBLICATIONS

Bocek, Thomas, et al., "Blockchains Everywhere—A Use-case of Blockchains in the Pharma Supply-Chain", 2017 International Symposium on Integrated Network and Service Management, Lisbon, Portugal, May 8-12, 2017, pp. 772-777.*

Kuo, Tsung-Ting, et al., "Blockchain distributed ledger technologies for biomedical and health care applications", Journal of the American Informatics Associations, Oxford University Press, vol. 24, No. 6, Sep. 8, 2017, pp. 1211-1220.*

Englehardt, Mark A., "Hitching Healthcare to the Chain: An Introduction to Blockchain Technology in the Healthcare Sector", Technology Innovation Management Review, vol. 7, Issue 10, Oct. 2017, 14 pages.*

(Continued)

*Primary Examiner* — Robert Stevens
(74) *Attorney, Agent, or Firm* — Andre J. Bahou; Christopher T. McNeill; Waller Lansden Dortch & Davis, LLP

(57) ABSTRACT

A computer-implemented method of auditing drug supply chain data gathered from a distributed ledger is disclosed. The method includes receiving a population of drug product records from the distributed ledger. The method includes receiving a first set of drug product criteria. The method includes determining a weighted probability for one or more drug product records of the population of drug product records. The method includes generating a randomized first subset of drug product records from the population of drug product records based on the weighted probability of the one or more drug product records. Other methods, systems, and the like for unbiased drug selection for audit are also disclosed.

20 Claims, 10 Drawing Sheets

(56) References Cited

OTHER PUBLICATIONS

"Distributed ledger", Wikipedia, downloaded from: https://en.wikipedia.org/wiki/Distributed_ledger, Jun. 24, 2021, pp. 1-2.*
"Blockchain", Wikipedia, downloaded from: https://en.wikipedia.org/wiki/Blockchain, Jun. 24, 2021, pp. 1-19.*

* cited by examiner

300

310  350

| Feature | Value |
|---|---|
| Product ID | 00473887 |
| Drug Name | Percocet |
| Expiration Date | 05/17/2019 |
| Location | Pennsylvania |
| Drug Schedule Classification | Schedule II |

312 — Product ID
314 — Drug Name
316 — Expiration Date
318 — Location
320 — Drug Schedule Classification 352 — 00473887
354 — Percocet
356 — 05/17/2019
358 — Pennsylvania
360 — Schedule II

FIG. 3

Receiving a population of drug product records from the distributed ledger
702

Receiving a first set of drug product criteria
704

Determining a weighted probability for each of the drug product records based on the first set of drug product criteria
706

Generating a randomized first subset of drug product records from the population of drug product records
708

Removing a second subset of drug product records from the population of drug product records
710

FIG. 7

UNBIASED DRUG SELECTION FOR AUDIT USING DISTRIBUTED LEDGER TECHNOLOGY

CROSS-REFERENCES TO RELATED APPLICATIONS

This application claims priority to U.S. Provisional Application No. 62/658,312 filed Apr. 16, 2018, titled "Unbiased Drug Selection for Audit Using Distributed Ledger Technology," which is incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND OF THE INVENTION

Governmental and other regulations of pharmaceutical products are burdensome on the companies who trade in pharmaceuticals and those who enforce the regulations. Some regulations require a periodic audit of pharmaceutical products. An auditor performing the audit, for example, may need a repeatable, defined, but flexible process for selecting samples from a population of pharmaceutical items eligible for audit. The conventional method for selecting pharmaceuticals for audit is a pure random sampling from the population of pharmaceutical products by random selection of pharmaceutical identification numbers. However, this is an inflexible solution that may create undue burden on smaller entities within the pharmaceutical supply chain and, in some cases, states with smaller human populations.

BRIEF SUMMARY

A computer-implemented method of auditing drug supply chain data gathered from a distributed ledger is disclosed. In one embodiment, the method may include receiving a population of drug product records from the distributed ledger. The method may include receiving a first set of drug product criteria. The method may include determining a weighted probability for one or more drug product records based on the first set of drug product criteria. The method may include generating a randomized first subset of drug product records from the population of drug product records based on the weighted probability of the one or more drug product records.

Another embodiment of a computer-implemented method of auditing drug supply chain data gathered from a distributed ledger is disclosed. In one embodiment, the method may include receiving a population of drug product records from the distributed ledger. The method may include receiving a first set of drug product criteria. The method may include determining a weighted probability for one or more drug product records based on the first set of drug product criteria. The method may include generating a randomized first subset of drug product records from the population of drug product records based on the weighted probability of the one or more drug product records. The method may include removing a second subset of drug product records from the population of drug product records.

Another embodiment of a computer-implemented method of auditing drug supply chain data gathered from a distributed ledger is disclosed. The method may include receiving a population of drug product records from the distributed ledger. The method may include receiving a first set of drug product criteria. The method may include determining a weighted probability for one or more drug product records based on the first set of drug product criteria. The method may include generating a randomized first subset of drug product records from the population of drug product records based on the weighted probability of the one or more drug product records. The method may include reducing the weighted probability of a first drug product record based on the first subset of drug product records. The method may include increasing the weighted probability of a second drug product record based on the first subset of drug product records.

BRIEF DESCRIPTION OF THE DRAWINGS

FIG. 3 is a schematic block view illustrating one embodiment of a drug product record for unbiased drug selection for audit.

FIG. 7 is a block flowchart diagram illustrating another embodiment of a method for unbiased drug selection for audit.

DETAILED DESCRIPTION

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

The phrases "in one embodiment," "in some embodiments," "in an embodiment," "in another embodiment," and the like, as used herein do not necessarily refer to the same embodiment or different embodiments, although they may, and mean "one or more but not all embodiments" unless expressly specified otherwise. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, or states. Thus, such conditional language is not generally intended to imply that features, elements or states are in any way required for one or more embodiments or that one or more embodiments necessarily include logic for deciding, with or without author input or prompting, whether these features, elements or states are included or are to be performed in any particular embodiment.

In the present specification "comprise" means "includes or consists of" and "comprising" means "including or consisting of." Furthermore, the term "based on" indicates the presence of an influence, but does not necessarily exclude the presence of other influences. Thus, the term "based on" means "based on, at least in part." An enumerated listing of items (e.g. "first," "second," "third," and the like) does not imply any order or that any or all of the items are mutually exclusive or mutually inclusive, unless expressly specified otherwise. The phrase "or" does not mean mutual exclusivity unless expressly stated, and, thus, means "and/or."

The present disclosure is directed to systems and methods for unbiased drug selection for audit using distributed ledger technology. These systems and methods may provide an auditor with a subset of pharmaceutical products from a population of auditable products. The subset may be selected from the population with reduced bias from the auditor. The subset may be selected from the population based on random chance, but the selection may not be based solely on random chance. Because of the unbiased but tailored selection process, the subset may a more fair sampling than a subset that may be produced by other methods.

Figure 1:
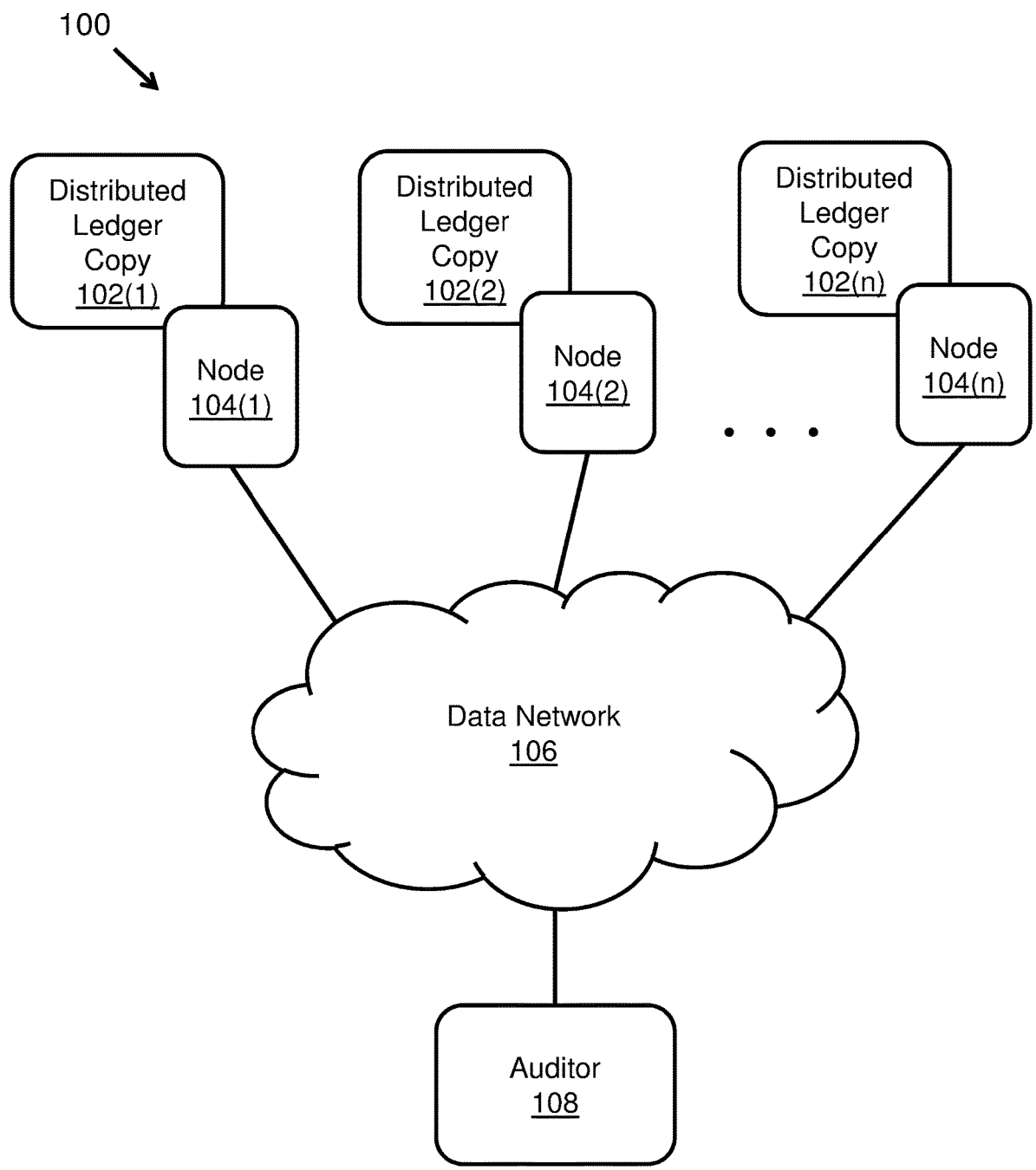
FIG. 1 is a schematic block view illustrating one embodiment of a system for unbiased drug selection for audit.

FIG. 1 depicts one embodiment of a system 100. The system 100 may include a system for unbiased drug selection for audit. The system 100 may include a distributed ledger. The distributed ledger may be replicated in one or more distributed ledger copies 102(1)-(n) on one or more computing devices called nodes 104(1)-(n). The one or more nodes 104(1)-(n) may be data communication with each other via a data network 106. Drug product population data may be stored on the distributed ledger copies 102(1)-(n). The system 100 may include an auditor 108. The auditor 108 may include a computing device that may receive drug product data from one or more distributed ledger copies 102(1)-(n) and use the drug product data to randomly select a sample of drug products for audit. The randomly selection of the auditor 108 may select the sample in a way that is fair, flexible, unbiased, and that takes into account realities of the drug product population.

The following description further describes one or more embodiments of the present disclosure. In one embodiment, the system 100 may include one or more distributed ledger copies 102(1)-(n). The one or more distributed ledger copies 102(1)-(n) may include a consensus of replicated and synchronized data spread across the one or more nodes 104(1)-(n). For example, in one embodiment the distributed ledger of the distributed ledger copies 102(1)-(n) may include a blockchain. In other embodiments, the distributed ledger may include some other implementation of a distributed ledger. The distributed ledger may include a portion of a distributed ledger platform (e.g., the distributed ledger may be hosted on the ETHERIUM blockchain platform provided by the Etherium Foundation) or may include its own separate distributed ledger. In one embodiment, the distributed ledger of the one or more distributed ledger copies 102(1)-(n) may include a permissioned distributed ledger. In another embodiment, the distributed ledger may include an unpermissioned distributed ledger.

In some embodiments, a node 104 may store the distributed ledger copy 102. In another embodiment, the distributed ledger copy 102 may be hosted or stored on another computing device and a node 104 may access the distributed ledger copy 102 remotely. In some embodiments, the distributed ledger copy 102 may store the drug product data on the distributed ledger copy 102. In other embodiments, the distributed ledger copy 102 may store a reference to drug product data, and a computing device may access the drug product data by using the reference. For example, the distributed ledger copy 102 may store a Uniform Resource Identifier (URI) and a hash of the drug product data. A computing device may access the drug product data using the URI and may use the hash to determine whether the drug product data has been modified since the reference was posted to the distributed ledger copy 102.

In some embodiments, a distributed ledger copy 102 may include population data. In one embodiment, the population data may include data describing all drug products from which the auditor 108 may select during an audit of pharmaceutical products. For example, in one embodiment, the population may include all drug products tracked by the auditor 108, tracked by an entity that operates the auditor 108, tracked by the nodes 104(1)-(n), tracked by the distributed ledger copies 102(1)-(n), or tracked by another entity. In one embodiment, the population may include a subset of all drug products tracked by the auditor 108. Other ways of determining a population of drug products are also included within the meaning of "population."

In some embodiments, the system 100 may include the one or more nodes 104(1)-(n). As used herein, the designation "node 104" refers to any of the nodes 104(1)-(n), and the designation "node 104(1)," "node 104(2)," or the like may refer to a specific node of the nodes 104(1)-(n) and may illustrate examples of interaction between two or more nodes of the nodes 104(1)-(n). A node 104 may include a desktop computer, laptop computer, server, tablet, phone, smartwatch, or other computing device.

In one embodiment, the data network 106 may include a network that provides data communication capabilities between computing devices. The data network 106 may include one or more devices that transmit data between devices. In one embodiment, the data network 106 may include one or more routers, switches, servers, computing devices, or the like. The data network 106 may include segments where the data transmission media is wired, such as Ethernet, or segments where the data transmission is wireless, such as cellular data, Wi-Fi, or the like. In some embodiments, the data network 106 may include the Internet, a wide area network (WAN), local area network (LAN), or other network.

A controller, processor, computing device, client computing device, or computer (all of which may be referred to herein as a "computing device") may include at least one or more processors or processing units and a system memory. The computing device may also include at least some form of computer-readable media. By way of example and not limitation, computer-readable media may include computer storage media or communication media. Computer-readable storage media may include volatile or nonvolatile, removable or non-removable media implemented in a method or technology that may enable storage of information, such as computer-readable instructions, data structures, program modules, files, databases or other data. Communication media may embody computer-readable instructions, data structures, program modules, or other data in a modulated data signal such as a carrier wave or other transport mechanism and include information delivery media. Those skilled in the art should be familiar with the modulated data signal, which may have one or more of its characteristics set or changed in such a manner as to encode information in the signal. Combinations of the above are also included within the scope of computer-readable media. As used herein, a server may include a computing device. A server may include an edge server, a plurality of data servers, a storage database (e.g., a large scale RAID array), or various networking components. A server may refer to a single computing device or multiple computing devices. It is contemplated that these devices or functions may also be implemented in virtual machines implemented on one or more physical computing devices.

In some embodiments, the system 100 may include an auditor 108. The auditor 108 may include a computing device. The computing device of the auditor 108 may be similar to a node 104. In some embodiments, the auditor 108 may include a distributed ledger copy 102. In one embodiment, the auditor 108 may receive from one or more nodes 104(1)-(n) the distributed ledger copy 102. In one embodiment, the auditor 108 may use data from the distributed ledger copy 102 to generate a list of drug products for a randomized audit. The auditor 108 may implement one or more of the methods described herein.

Figure 2:
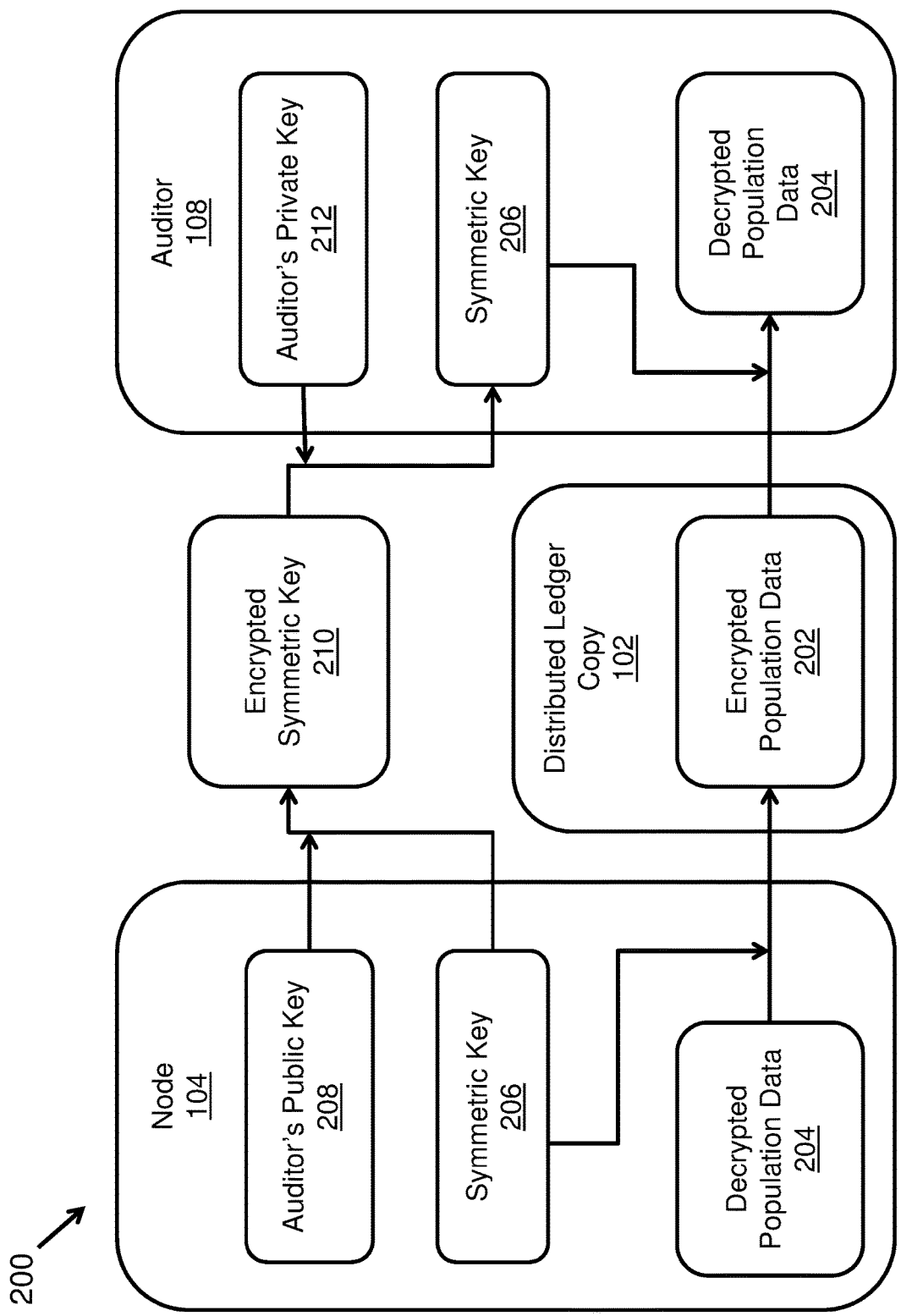
FIG. 2 is a schematic block view illustrating one embodiment of a system for unbiased drug selection for audit.

FIG. 2 depicts one embodiment of a system 200. In one embodiment, the population data of a distributed ledger copy 102 may be encrypted as encrypted population data 202. A node 104 may include decrypted population data 204. The decrypted population data 204 may include population data that has not yet been encrypted. The node 104 may encrypt the decrypted population data 204 to generate encrypted population data 202 and insert it into a distributed ledger copy 102. The auditor 108 may receive the encrypted population data 202. To use the population data 202, the auditor 108 may decrypt the population data to generate decrypted population data 204. The node 104 or auditor 108 may use one or more encryption methods. For example, the node 104 or auditor 108 may use symmetric key encryption (for example, Advanced Encryption Standard (AES)) or asymmetric key encryption (for example, a public-key infrastructure such as RSA).

For example, as shown in FIG. 2, the node 104 may encrypt decrypted population data 204 with a symmetric key 206 to form encrypted population data 202. The node 104 may send the encrypted population data 202 to the distributed ledger copy 102. In some embodiments, the node 104 may send the encrypted population data 202 to the auditor 108. The node 104 may encrypt the symmetric key 206 using the auditor's public key 208 to generate the encrypted symmetric key 210. The node 104 may send the encrypted symmetric key 210 to the auditor 108. The node 104 may send the encrypted population data 202 or the encrypted symmetric key 210 via the data network 106 of FIG. 1. The auditor 108 may receive the encrypted symmetric key 210 and may decrypt the encrypted symmetric key 210 using the auditor's private key 212. In response to having the symmetric key 204, the auditor 108 may decrypt the encrypted population data 202 into decrypted population data 204.

It should be noted that, in some embodiments, the encrypted population data 202 or the decrypted population data 204 may include a portion of the drug population data and may not include the entire drug population data.

FIG. 3 depicts one embodiment of a drug product record 300. A drug product record 300 may include data about a drug product in the population. The drug product record 300 may include data about a drug product at a certain time. In one embodiment, the population data stored in the encrypted population data 202 of a distributed ledger copy 102 or stored in the decrypted population data 204 of a node 104 or the auditor 108 may include one or more drug product records 300. In some embodiments, the encrypted population data 202 may store transactions (e.g., blockchain transactions) that include drug product data, and the auditor 108 may generate the population of drug product records 300 using the transactions from the distributed ledger copy 102.

In one embodiment, a drug product record 300 may include one or more drug product features 310. In one embodiment, a drug product feature 310 may include a category of information about a drug product. In one embodiment, the drug product record 300 may include one or more drug product values 350. A drug product value 350 may include a value that corresponds to a drug product feature 310. In some embodiments, a plurality of drug product values 350 may correspond to a single drug product feature 310.

As an example of a drug product record 300, as depicted in FIG. 3, the one or more drug product features 310 may include a "Product ID" drug product feature 312. The one or more drug product values 350 may include a corresponding drug product value 352 of "00473887." The drug product value 352 may include a string of text or other form of data that may uniquely identify the drug product that corresponds to the drug product record 300. The drug product value 352 may be assigned by a government entity, a manufacturer, or other entity. The one or more drug product features 310 may include a "Drug Name" drug product feature 314. The one or more drug product values 350 may include a corresponding drug product value 354 of "Percocet." The drug product value 354 may include a brand name, generic name, or other name for the drug product that corresponds to the drug product record 300.

In some embodiments, the one or more drug product features 310 may include an "Expiration Date" drug product feature 316. The one or more drug product values 350 may include a corresponding drug product value 356 of "05/17/2019." The drug product value 356 may include a value corresponding to a time or date that the drug product of the drug product record 300 may expire. In some embodiments, the drug product record 300 may include other drug product features 310 that include a time or a date, such as a sell-by date. The one or more drug product features 310 may include a "Location" drug product feature 318. The one or more drug product values 350 may include a corresponding drug product value 358 of "Pennsylvania." In one embodiment, the drug product value 358 may include one or more location types. A location type may include a country; a state, province, or other national subdivision; a state/province subdivision such as a county; a city; a building; a room of a building; or other location data. The one or more drug product features may include a "Drug Classification Schedule" drug product feature 320. The one or more drug product values 350 may include a corresponding drug product value 360 of "Schedule II." The drug product value 360 may include text or other data classifying a drug product according to one or more drug classification systems. A classification system may include a system from a government entity, commercial entity, or other entity.

In one embodiment, the drug product record 300 may include other drug product features 310 and corresponding drug product values 350 not described above. In some embodiments, a drug product record 300 may include a drug product feature 310 that does not include a corresponding drug product value 350. The corresponding drug product value 350 may not be included in response to the corresponding value being missing, unknown, not applicable to the drug product record 300, or for other reasons.

Figure 4:
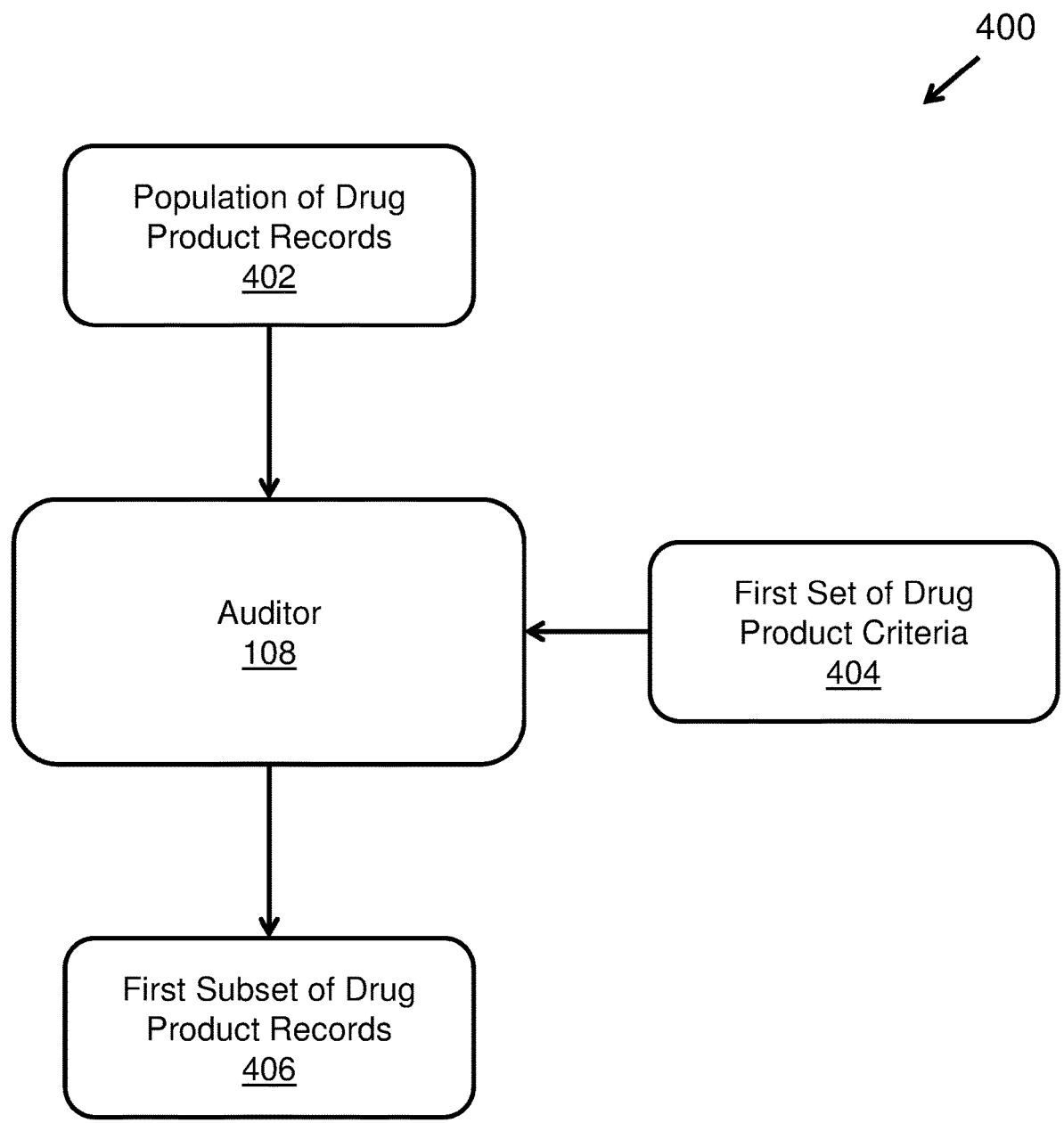
FIG. 4 is a schematic block view illustrating one embodiment of a system for unbiased drug selection for audit.

FIG. 4 depicts one embodiment of a system 400. The system 400 may include a population of drug product records 402. The population of drug product records 402 may include the decrypted population data 204 of FIG. 2. The population of drug product records 402 may include data about one or more drug product records 300. The population of drug product records 402 may include a plurality of drug product records 300 that may correspond to auditable drug products. The system 400 may include the auditor 108. The auditor 108 may receive the population of drug product records 402. In another embodiment, the system 400 may include a first set of drug product criteria 404. The first set of drug product criteria 404 may include input transmitted from a peripheral device (e.g. a mouse, keyboard, scanner, or the like) of the auditor 108. The first set of drug product criteria 404 may include data transmitted from a node 104 via the data network 106. The node 104 may transmit the data in response to a user command from the auditor 108, the node 104, or the like. In one embodiment, the first set of drug product criteria 404 may include data read from a file indicated by a user. The first set of drug product criteria 404 may include a configuration or data stored by the auditor 108 and configured to randomly select one or more drug product records 300 for audit. The auditor 108 may receive the population of drug product records 402 and first set of drug product criteria 404 and, in response, randomly select a first subset of drug product records 406 for audit. The auditor 108 may select the first subset of drug product records 406 according to one or more methods described herein.

Figure 5A:
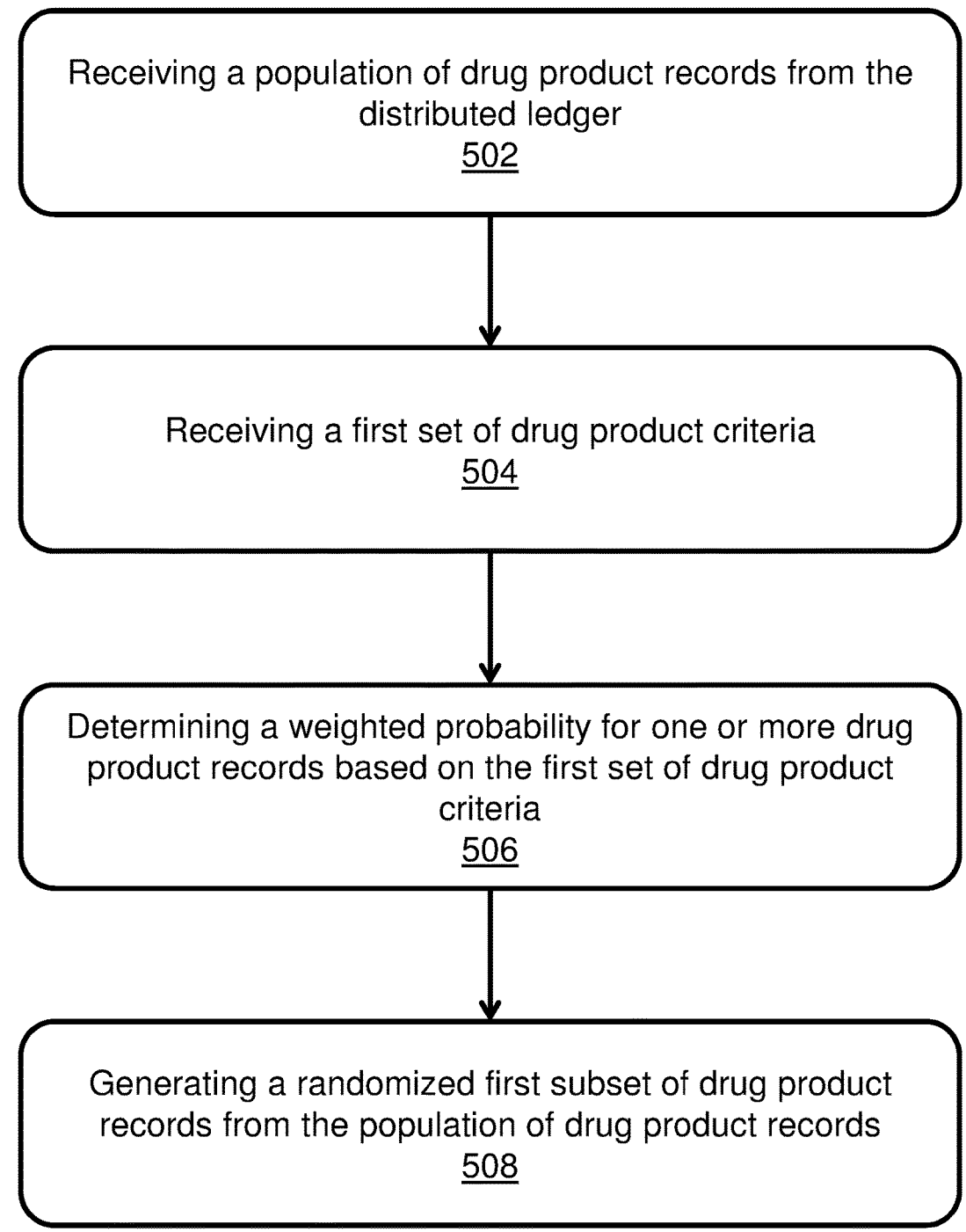
FIG. 5A is a block flowchart diagram illustrating one embodiment of a method for unbiased drug selection for audit.

FIG. 5 depicts one embodiment of a method 500. The method 500 may include a computer-implemented method of auditing drug supply chain data gathered from a distributed ledger. In one embodiment, the method 500 may include receiving 502 a population of drug product records from the distributed ledger. The method 500 may include receiving 504 a first set of drug product criteria. The method 500 may include determining 506 a weighted probability for one or more drug product records of the population of drug product records based on the first set of drug product criteria. The method 500 may include generating 508 a randomized first subset of drug product records from the population of drug product records. The generating 508 may be based on the weighted probability of the one or more drug product records.

In some embodiments, the distributed ledger may include the distributed ledger copy 102 of FIG. 1. The population of drug product records may include the population of drug product records 402 of FIG. 4, the encrypted population data 202 of FIG. 2, or other population data. The population data may include one or more drug product records 300 as depicted in FIG. 3.

In one embodiment, receiving 502 the population of drug product records from the distributed ledger may include receiving, at the auditor 108, one or more drug product records 300 from the distributed ledger. Receiving 502 the population of drug product records from the distributed ledger may include assembling the population of drug product records 402 from the received one or more drug product records 300. For example, the auditor 108 may portions of the distributed ledger copy 102 from one or more nodes 104(1)-(n) over the data network 106 and decrypt encrypted population data 202. The auditor 108 may gather the decrypted portions of the distributed ledger copy 102 to assemble the population of drug product 402. As used herein, the term "population of drug product records 402" may include all the drug product records 300 corresponding to drug products that may be candidates for an audit. In another embodiment, receiving 502 a population of drug product records from the distributed ledger may include receiving the distributed ledger copy 102 (e.g., from a node 104, a server, or the like) or retrieving the population of drug product records 402 (e.g., from a file, a computing device, or the like). Receiving 502 a population of drug product records from the distributed ledger may include downloading the population of drug product records 402.

In some embodiments, receiving 504 the first set of drug product criteria may include receiving the first set of drug product criteria from user input. Receiving the first set of drug product criteria from user input may include detecting the user input, processing the user input, converting the user input into computer-readable data or commands, or other data-receiving steps. The auditor 108 may receive the user input. In some embodiments, receiving 504 the first set of drug product criteria may include receiving the first set of drug product criteria from a file (e.g., stored on the auditor 108) or from a remote computing device (e.g., via the data network 106).

In one embodiment, the first set of drug product criteria 404 may include a drug product feature 310, a drug product value 350, an instruction, or other data. An instruction may include an instruction executable by a computing device, such as program code, a script, or other executable instructions. In one embodiment, an instruction of the first set of drug product criteria may include user input. The user input may indicate how to adjust the weighted probability of a drug product record 300. For example, a user may indicate that the drug product feature 318 "Location" is twice as weighted as the drug product feature 314 "Drug Name," the drug product feature 318 "Location" includes 20% of the total weighted probability, or other weighting indications. In some embodiments, an instruction may indicate that the weighted probability of a drug product record 300 may increase in response to a certain drug product value 350 of a drug product feature 310. For example, a user may indicate that drug product records 300 with a drug product value 360 of "Schedule II" have a higher weighted probability than a drug product record 300 with a drug product value 360 of "Schedule V." In another example, in one embodiment, a user may indicate that the first set of drug product criteria 404 includes the drug product feature 318 "Location" and an instruction to adjust the weighted probability of a drug product record 300 based on the human population of the drug product value 358 of "Location."

In some embodiments, a drug product record 300 may include a weighted probability. The weighted probability may not be included in the data of the drug product record 300 like a drug product feature 310 or drug product value 350 may be. The weighted probability of the drug product record 300 may reflect how likely the drug product record 300 is to be selected for audit. In another embodiment, the weighted probability may be expressed as a decimal number (e.g., 0.18), a percentage (4.8%), a fraction (1/37), or another notation.

In one embodiment, a weighted probability of a drug product record 300 may include a base weight. The base weight may include a default or predetermined weight. The base weight for each drug product record 300 may include a weight equal to or similar to other drug product records 300 of the population of drug product records 402. An equal base weight for each drug product record 300 may indicate that each drug product record 300 has an equal chance of being randomly selected for audit. In one embodiment, a base weight may include another type of base or default probability.

In some embodiments, a weighted probability for a drug product record 300 may be adjusted (e.g., increased or decreased) based on a drug product feature 310 or drug product value 350 of the drug product record 300, a drug product feature 310 or drug product value 350 of the first set of drug product criteria, an instruction of the first set of drug product criteria, or other data. The weighted probability of a drug product record 300 may be larger in response to the drug product record 300 including a drug product value 350 that occurs more often in the population of drug product records 402. For example, the first set of drug product criteria may include the drug product feature 318 "Location" and an instruction to adjust the weighted probability of a drug product record 300 of the population of drug product records 402 in response to the drug product value 358 corresponding to a location with a higher portion of the human population. In response, determining 504 the weighted probability for one or more drug product records may include increasing the weighted probability for a drug product record 300 whose drug product value 358 for location includes a location with a larger human population or portion of the human population. In some embodiments, determining 504 the weighted probability for one or more drug product records may include decreasing the weighted probability for a drug product record 300 whose drug product value 358 for location includes a location with a smaller human population or portion of the human population. In some embodiments, other drug product criteria may be used to similarly adjust the weighted probability of a drug product record 300 based on a size or portion. For example, the first set of drug product criteria may include a drug product feature 310 for "Level in the Supply Chain." The weighted probability for a drug product record 300 may be larger in response to the drug product record 300 including a level in the supply chain with more drug products, with more entities at that level of the supply chain, where drug products spend more time, or the like. Other drug product features 310 such as drug name 314, drug classification schedule 320, or other drug product features 310 may be used.

In one embodiment, the first set of drug product criteria may include the expiration date drug product feature 316 and an instruction to increase the weighted probability of drug product records 300 that include a drug product value 356 with an earlier expiration date, later expiration date, or other type of expiration date. In some embodiments, the first set of drug product criteria 404 may include multiple drug product features 310, drug product values 350, instructions, or other data.

In another embodiment, determining 506 the weighted probability for each drug product record may include calculating the weighted probability for each drug product feature 310 or value 350. Calculating a weighted probability may include using one or more inputs, such as user input, population of drug product records 402, or other data and processing or operating on the inputs according to functionality of the auditor 108. As described below, the functionality of the auditor 108 may include software (including one or more program instructions), hardware (such as circuits or the like) or a combination of both. Processing the input may include producing a weighted probability as an output.

In some embodiments, generating 508 the randomized first subset of drug product records may include generating the first subset of drug product records 406 to include a predetermined number of drug product records 300. The first subset of drug product records 406 may include a predetermined number of drug product records 300. In one embodiment, a user may input a predetermined number for the size of the first subset of drug product records 406. The predetermined number of the size of the first subset of drug product records 406 may be based on a computer configuration, a file, or the like. In one embodiment, generating 508 the randomized first subset of drug product records may include random number generation, pseudo-random number generation, or the like.

In some embodiments, generating 508 the randomized first subset of drug product records may include selecting a drug product record 300. The selection may include a random selection where the probability of the drug product record 300 being selected may be based on the weighted probability of the drug product record 300. The random selection may include a drug product record 300 with a higher weighted probability having more of a probability of selection for audit than a drug product record 300 with a lower weighted probability.

Figure 5B:
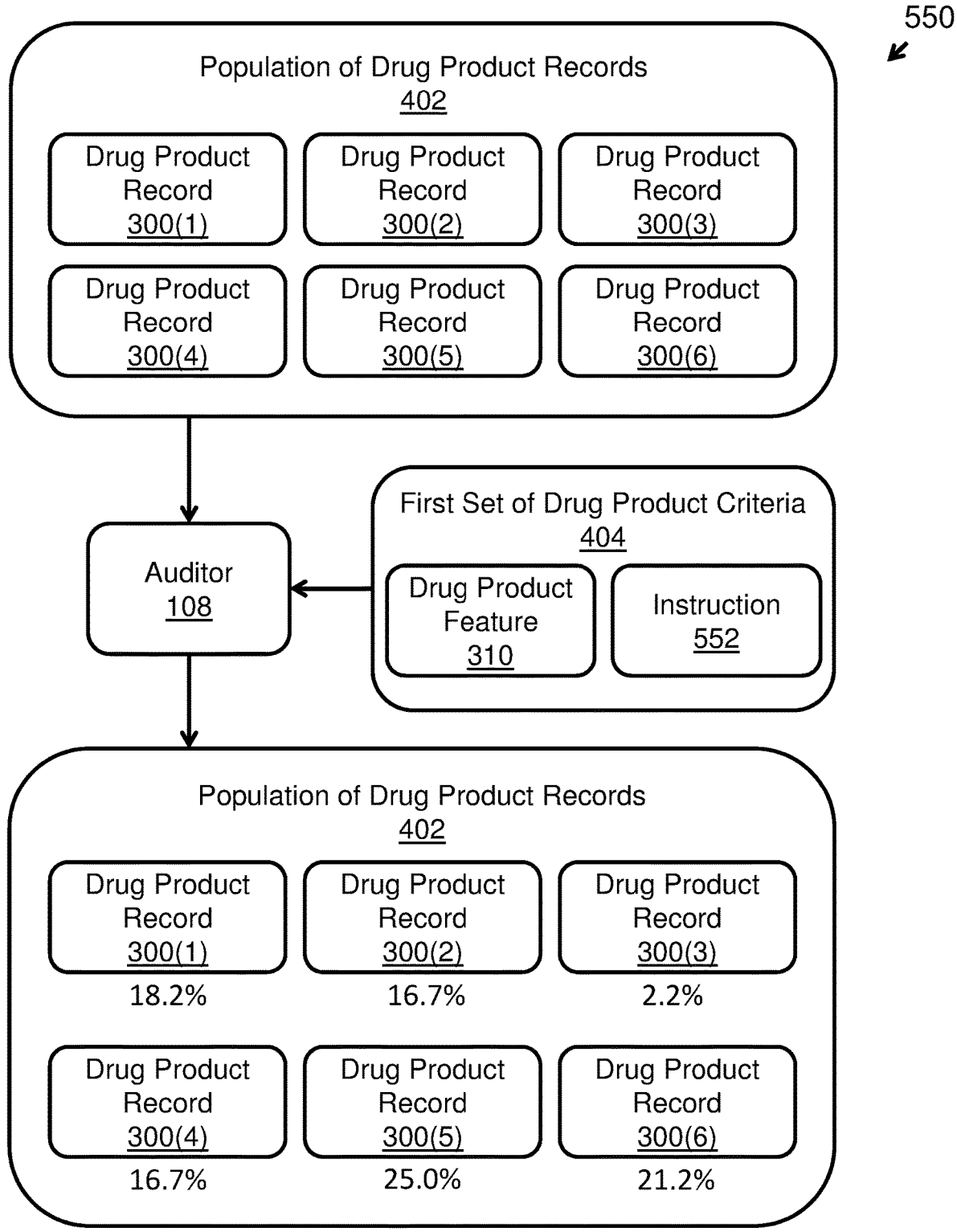
FIG. 5B is a block flowchart diagram illustrating another embodiment of a method for unbiased drug selection for audit.
Figure 5C:
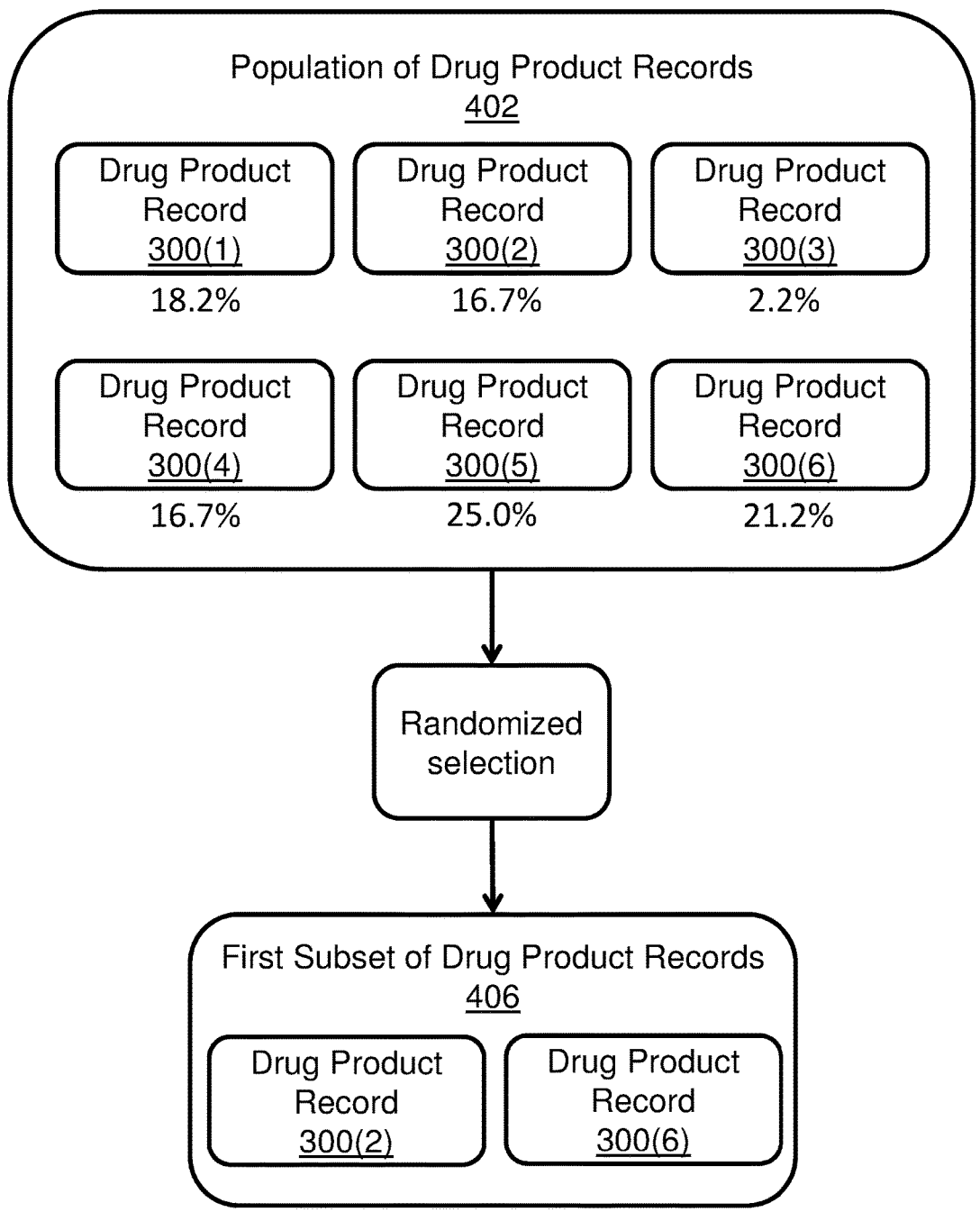
FIG. 5C is a block flowchart diagram illustrating another embodiment of a method for unbiased drug selection for audit.

FIG. 5B and FIG. 5C depict one embodiment of a system 550. FIG. 5B and FIG. 5C may depict the state of certain elements of the system 400 of FIG. 4 and different points in time during the occurrence of the method 500 or other methods described herein. The system 550 may include components similar to components depicted in other Figures such as the population of drug product records 402, one or more drug product records 300(1)-(6), the auditor 108, the first set of drug product criteria 404, or the firsts subset of drug product records 406.

As depicted in the example of FIG. 5B, the population of drug product records 402 may include six drug product records 300(1)-(6). The auditor 108 may receive 502 the population of drug product records. The auditor 108 may receive 504 the first set of drug product criteria. In this example, the first set of drug product criteria 404 may include a drug product feature 310 and an instruction 552. The auditor 108 may determine 506 the weighted probability for the drug product records of the population of drug product records based on the first set of drug product criteria. As a result, each drug product record 300 may include a weighted probability, displayed below each drug product record 300 in the population of drug product records 402.

As depicted in the example of FIG. 5C, the auditor may apply a randomized selection to the population of drug product records 402. The randomized selection may include the auditor 108 generating 508 the randomized first subset of drug product records. As a result, the first subset of drug product record 406 may include two of the drug product records 300(1)-(6) of the population of drug product records 402, namely, drug product records 300(2) and 300(6).

In another embodiment, generating 508 the randomized first subset of drug product records may include repeatedly generating a portion of the first subset of drug product records 406. Generating 508 the randomized first subset of drug product records may include adjusting the weighted probabilities of the drug product record 300 of the first set of drug product criteria in between generating portions of the first subset of drug product records 406. In other words, as the first subset of drug product records 406 is randomly selected, the weighted probabilities of one or more drug product records 300 may change. In one embodiment, generating 508 the randomized first subset of drug product records may include the first subset 406 including only a predetermined number of drug product records 300 with a certain drug product value 350 for a certain drug product feature 310. The drug product value 350 or drug product feature 310 may be based on user input. For example, user input may include that only 100 drug product records of the first subset of drug product records 406 may include "Percocet" as the drug product value 354 for "Drug Name."

Generating 508 the randomized first set of drug product records based on weighted probability may result in a set of drug products for audit that is more fair than a conventional randomized sample of drug products. Because the randomization of the present disclosure can take into account realities about the drug product population, such as the human populations of locations being different in size or drug products spending different amounts of time at different levels in the supply chain, without including biases of a human auditor or the like, the randomization present disclosure results a more representative sample that may improve the quality of drug product audits.

In some embodiments, generating 508 the randomized first subset of drug product records may include presenting the first subset of drug product records 406 to a user. Presenting the first subset of drug product records 406 may include displaying certain drug product values 350 of the drug product records 300 such as product ID, user-specified drug product features of the first subset of drug product records 406, or the like. Presenting information about the first subset of drug product records 406 may allow a user to verify that the first subset of drug products records 406 conforms to a certain criteria for selecting a sample for an audit. It may also allow a user to adjust one or more configurations of the audit to adjust subsequent audits.

Figure 6:
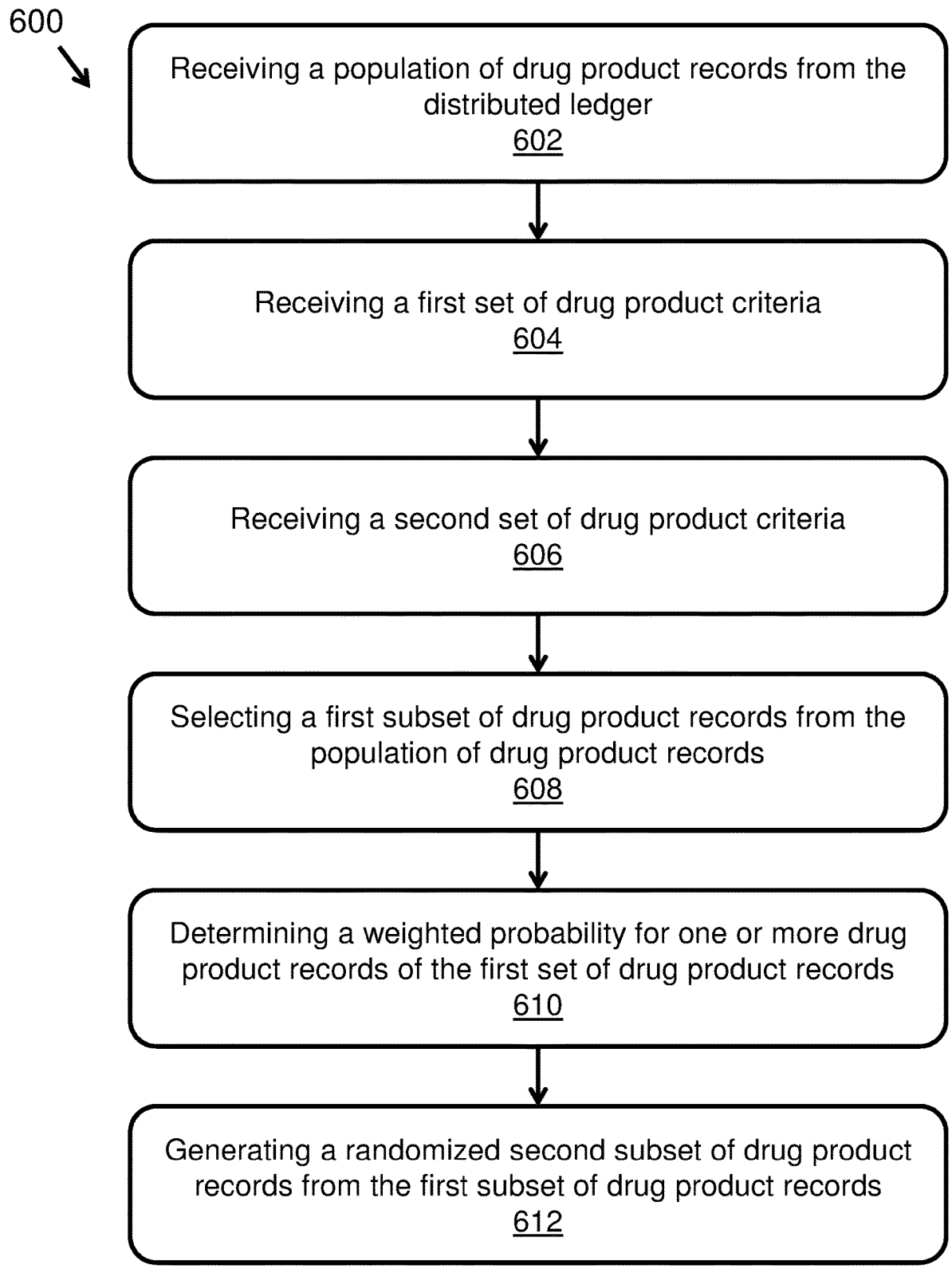
FIG. 6 is a block flowchart diagram illustrating another embodiment of a method for unbiased drug selection for audit.

FIG. 6 depicts one embodiment of a method 600. The method 600 may include a computer-implemented method of auditing drug supply chain data gathered from a distributed ledger. In one embodiment, the method 600 may include receiving 602 a population of drug product records from the distributed ledger. Receiving 602 the population of drug product records from the distributed ledger may be similar to receiving 502 the population of drug product records from the distributed ledger of the method 500 of FIG. 5. In some embodiments, the method 600 may include receiving 604 a first set of drug product criteria. In some embodiments, the method 600 may include receiving 606 a second set of drug product criteria. Receiving 604, 606 the first set and second set of drug product criteria may be similar to receiving 504 the first set of drug product criteria of the method 500 of FIG. 5.

In one embodiment, the method 600 may include selecting 608 a first subset of drug product records from the population of drug product records based on the first set of drug product criteria. In one embodiment, selecting 608 a first subset of drug product records based on the first set of drug product criteria may include selecting only drug product records with a specified drug product value 350 for a specified drug product feature 310. For example, the first set of drug product criteria may include the drug product feature 318 "Location" and an instruction that only drug product records 300 with a drug product value 358 of "California" are candidates for a randomized drug audit. In response, the first subset of drug product records 406 may include only drug product records 300 with the drug product value 350 of "California" for the drug product feature 318 of "Location." In one embodiment, selecting 608 the first subset of drug product records based on the first set of drug product criteria may include selecting only drug product records 300 with certain drug product value 350, range of values 350, or the like for one or more drug product features 310. In some embodiments, selecting 608 the first subset of drug product records based on the first set of drug product criteria may include selecting drug product records 300 that do not include a certain drug product value 350 for a drug product feature 310. For example, a user may input the value "Schedule II" to indicate that the only drug product records 300 without the drug product value 360 "Schedule II" for the drug product feature 320 "Drug Schedule Classification" are candidates for a randomized drug audit. In one embodiment, selecting 608 the first subset of drug product records based on the first set of drug product criteria may include other ways of selecting drug product records 300 from the population of drug product record 402. In other words, in one embodiment, the first set of drug product criteria 404 may be called a set of narrowing criteria because it may narrow down the candidates for audit before determining the weighted probabilities.

In one embodiment, the method 600 may include determining 610 a weighted probability for one or more drug product records of the first subset of drug product records based on the second set of drug product criteria. Determining 610 the weighted probability may be similar to determining 506 the weighted probability for one or more drug product records of the method 500 of FIG. 5. However, in one embodiment, determining 610 the weighted probability for the one or more drug product records may only determine the weighted probabilities of the first subset of drug product records 406 (i.e., those drug product records 300 not removed from candidacy based on the first set of drug product criteria 404).

In one embodiment, determining 610 the weighted probability for one or more of the drug product records may be based the absence of some drug product records 300 from the first subset of drug product records 406. For example, in one embodiment, the weighted probability for the drug product records 300 may be higher for drug product records 300 with drug product values 350 of states with a higher portion of the human population. In this example, the first set of drug product criteria 404 may include the drug product feature 318 "Location" and an instruction to exclude all drug product records 300 except those with a drug product value 358 of "Ohio," "Indiana," and "Michigan" from the first subset of drug product records 406. In response, each state's corresponding proportion of the human population for the group of states in the first subset of drug product records 406 may change and the weighted probability for the drug product records 300 may change. In some embodiments, the weighted probabilities of the drug product records of the first subset of drug product records 406 may change based on excluded drug product records 300.

In one embodiment, the method 600 may include generating 612 a randomized second subset of drug product records from the first subset of drug product records. Generating 612 the randomized second subset of drug product records from the first subset of drug product records may be similar to generating 508 the randomized first subset of drug product records from the population of drug product records of the method 500 of FIG. 5. In response, the method 500 may generate an audit list of drug products that is more specialized or specific than the method 500 of FIG. 5, but may still include the benefits of being unbiased, flexible, and fair.

In one embodiment, the auditor 108 may use the first set of drug product criteria 404 before the second set of drug product criteria. In one embodiment, receiving 606 the second set of drug criteria may occur before receiving 604 the first set of drug product criteria. In some embodiments, receiving 604 the first set of drug product criteria and receiving 606 the second set of drug product criteria may include receiving different portions of each set at different times (e.g., receiving some portions of the first set 404 before receiving some portions of the second set). In one embodiment, the first set of drug product criteria 404 may include the same drug product criteria as the second set of drug product criteria. In one embodiment, the first set of drug product criteria 404 and the second sets of drug product criteria may share some, but not all, drug product criteria. In some embodiments, the first set of drug product criteria 404 and the second set of drug product criteria may not share any drug product criteria.

FIG. 7 depicts one embodiment of a method 700. The method 700 may include a computer-implemented method of auditing drug supply chain data gathered from a distributed ledger. In one embodiment, the method 700 may include receiving 702 a population of drug product records from the distributed ledger. Receiving 702 the population of drug product records from the distributed ledger may be similar to receiving 502 the population of drug product records from the distributed ledger of FIG. 5. In one embodiment, the method 700 may include receiving 704 a first set of drug product criteria. Receiving 704 the first set of drug product criteria may be similar to receiving 504 the first set of drug product criteria of the method 500 of FIG. 5.

In one embodiment, the method 700 may include determining 706 a weighted probability for one or more drug product records of the populations of drug product records based on the first set of drug product criteria. Determining 706 the weighted probability of the one or more the drug product records may be similar to determining 506 the weighted probability for one or more drug product records of the method 500 of FIG. 5. In one embodiment, the method 700 may include generating 708 a randomized first subset of drug product records from the population of drug product records based on the weighted probability of the one or more drug product record. Generating 708 the randomized first subset of drug product records from the population of drug product records may be similar to generating 508 the randomized first subset of drug product records of the method 500 of FIG. 5.

In one embodiment, the method 700 may include removing 710 a second subset of drug product records from the population of drug product records. As used herein, the term "removing," when used in relation to a drug product record 300 and the population of drug product records 402, may include excluding one or more drug product records 300 from candidacy for random selection. The exclusion may include a temporary exclusion or a permanent exclusion. The term may not include removing the one or more drug product records 300 or the data associated with them from the population of drug product records 402 stored in the encrypted population data 202 of a distributed ledger copy 102.

In some embodiments, removing 710 the second subset of drug product records may include removing the second subset of drug product records 300 based on the first set of drug product criteria 404. Removing 710 the second subset of drug product records may include removing the second subset of drug product records 300 based on the first subset of drug product records 406. In one embodiment, removing 710 the second subset of drug product records from the population of drug product records may include determining the weighted probability of the second subset of drug product records 300 to be 0. In some embodiments, removing 710 a second subset of drug product records from the population of drug product records may include logically removing the second subset of drug product records 300 from the population of drug product record 402.

In some embodiments, the second subset of drug product records 300 may include drug product records 300 with a same or similar drug product value 350 or value range as a drug product record 300 in the first subset of drug product records 406 or a drug product value 350 indicated by a drug product feature 310 of the first set of drug product criteria 404. For example, the first set of drug product criteria 404 may include the drug product feature 318 "Location" and may include an instruction to place drug product records 300 with the same location values 358 as those in the first subset of drug product records 406 in the second subset of drug product records 300. In response to generating 708 the randomized first subset of drug product records, the first subset of drug product records 406 may include drug product records 300 that include four drug product values 358 for "Location:" "Nevada," "Hawaii," "Florida," or "New Jersey." Thus, based on the first set of drug product criteria 404, removing 710 the second subset of drug product records from the population of drug product records may include removing all drug product records 300 with a drug product value 358 of "Nevada," "Hawaii," "Florida," or "New Jersey" from the population of drug product records 402. In response, the next iteration of the method 700, generating 708 the randomized first subset of drug product records from the population of drug product records may not include randomly selecting drug product records 300 with a drug product value 358 of "Nevada," "Hawaii," "Florida," or "New Jersey."

In one embodiment, the method 700 may include receiving a time period. Receiving the time period may include receiving the time period from user input, a file, a remote computing device, or other source. The time period may include a time interval over which an audit may occur. The time period may include subdivisions of time. In some embodiments, the time period received may be a subdivision of time of a larger time period. In some embodiments, each subdivision of time may include a time interval over which a sub-audit may occur. For example, in one embodiment, the time period may include one year. An audit may occur over the year specified by the time period. The time period of one year may include twelve subdivisions of one month each. Over each month, a sub-audit may occur. Continuing the example above, in the first one month subdivision, the sub-audit may only include drug product records 300 with drug product values 358 of "Nevada," "Hawaii," "Florida," or "New Jersey." In response, for the next iteration of the method 700 corresponding to the second one-month subdivision, generating 708 a randomized first subset of drug product records from the population of drug product records may not include randomly selecting drug product records 300 with a drug product value 358 of "Nevada," "Hawaii," "Florida," or "New Jersey."

In some embodiments, time periods or subdivisions of time period may include equal amounts of time in each respective time period or subdivisions of time period. In one embodiment, some time periods or subdivisions of a time period may include different amounts of time.

In one embodiment, the method 700 may include reinserting the second subset of drug product records 300 into the population of drug product records 402 in response to the time period expiring. As used herein, the term "expire" when referring to a time period or a subdivision of a time period may not necessarily mean that the time period has actually expired. In one embodiment, the time period expiring may include finishing generating the randomized first subset of drug product records 406 for the time period, subdivision of a time period, or the like. Thus, in response to finishing generating the randomized first subset of drug product records 406, the previously removed drug product records 300 may reinsert into the population of drug product records 402 and a new iteration of generating a randomized first subset of drug product records 406 may begin or be ready to begin.

In one embodiment, the method 700 may include selecting a subset of the population of drug product records 402 based on one or more drug product criteria, determining a weighted probability for each of one or more drug product records 300, and generating a randomized second subset of drug product records 300 based on the weighted probabilities, similar to the method 600 of FIG. 6.

Figure 8:
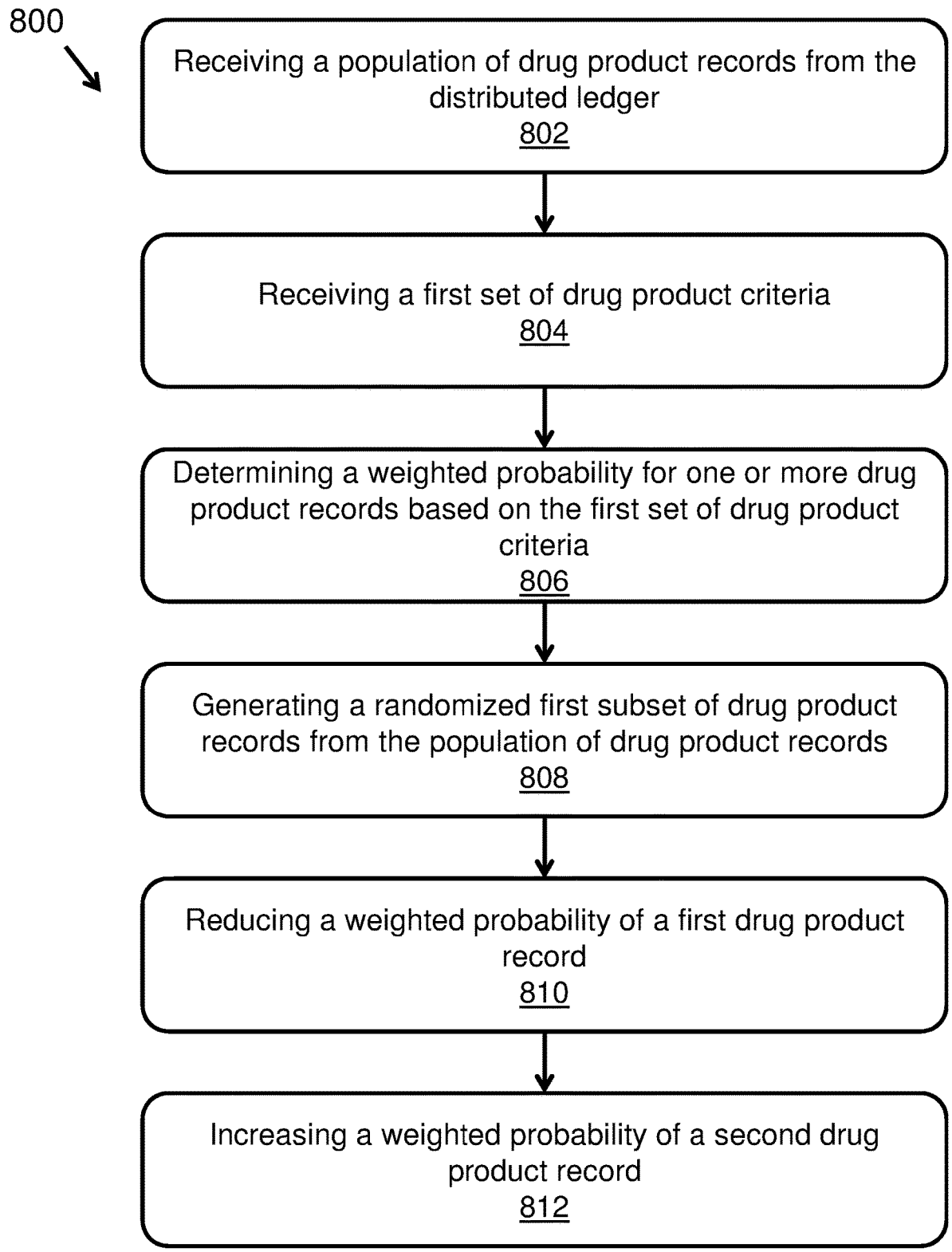
FIG. 8 is a block flowchart diagram illustrating another embodiment of a method for unbiased drug selection for audit.

FIG. 8 depicts one embodiment of a method 800. The method 800 may include a computer-implemented method of auditing drug supply chain data gathered from a distributed ledger. In one embodiment, the method 800 may include receiving 802 a population of drug product records from the distributed ledger. Receiving 802 the population of drug product records from the distributed ledger may be similar to receiving 502 the population of drug product records from the distributed ledger of FIG. 5. In one embodiment, the method 800 may include receiving 804 a first set of drug product criteria. Receiving 804 the first set of drug product criteria may be similar to receiving 504 the first set of drug product criteria of the method 500 of FIG. 5. In one embodiment, the method 800 may include determining 806 a weighted probability for one or more drug product records of the population of drug product records based on the first set of drug product criteria. Determining 806 the weighted probability for each of the drug product records may be similar to determining 506 the weighted probability for one or more drug product records of the method 500 of FIG. 5. In some embodiments, determining 806 the weighted probability for one or more drug product records may include determining a weighted probability based on an increase or decrease of a weighted probability of a drug product record 300, as described below. In one embodiment, the method 800 may include generating 808 a randomized first subset of drug product records from the population of drug product records based on the weighted probability of the one or more drug product records. Generating 808 the randomized first subset of drug product records be similar to generating 508 the randomized first subset of drug product of the method 500 of FIG. 5.

In one embodiment, the method 800 may include reducing 810 the weighted probability of a first drug product record based on the first subset of drug product records. In some embodiments, the method 800 may include increasing 812 a weighted probability of a second drug product record based on the first subset of drug product records. In one embodiment, the reduced or increased weighted probabilities may be used during a subsequent drug product audit (i.e., the weighted probabilities may not reset as may occur in some embodiments of the methods for auditing drug supply chain data described herein).

In one embodiment, reducing 810 the weighted probability of a first drug product record may include subtracting the weighted probability of the drug product record 300 by a predetermined amount, a specified portion of the weighted probability, or the like. Increasing 812 the weighted probability of a second product record may include adding a predetermined amount, a specified portion of the probability, or the like to the weighted probability.

For example, the first drug product criteria 404 may include a drug product feature 318 for "Location." The first subset of drug product records 406 may include drug product records 300 with twenty different drug product values 358 for "Location." In response, reducing 810 the weighted probability of the first drug product record may include reducing the weighted probability of drug product records 300 that include a drug product value 358 that match one of the twenty values 358 of the first subset of drug product records 406. Increasing 812 the weighted probability of a second product record may include increasing the weighted probability of drug product records 300 that include a drug product value 358 for "Location" that do not match the twenty values 358 of the first subset of drug product records 406.

In one embodiment, determining 806 the weighted probability of a drug product record may include calculating the weighted probability according to the equation $P_i(a, b, \ldots, j)$ where i is the drug product record 300 and a, b, $\ldots$, j include one or more drug product criteria 310, such as the first drug product criteria 404. Reducing 810 the weighted probability of the first drug product record may include calculating a new weighted probability $P'_i$ according to the equation $P'_i = P_i - (q/x)$ where q may include a fairness factor and x may include the number of drug product records 300 in the first subset of drug product records 406. In one embodiment, $P_u$ may include the weighted probability of a drug product record 300 u that was not selected in step 808 (e.g., a drug product record 300 in the second subset of drug product records 300). Increasing 812 the weighted probability may include increasing $P_u$ by $$\sum_{i}^{N-X} \frac{Pi - P'i}{n-x}$$

where N is the population of drug product records 402, X is the first subset of drug product records 406, and n is the number of drug product records in the population of drug product record 402. In other words, the weighted probability of a drug product record 300 of the second subset of drug product records 300 (e.g., a drug product record 300 that was not selected for audit) may be increased by a factor of the total reduced weighted probability of the first subset of drug product record 406 divided by the number of drug product records in the second subset of drug product record 300.

In one embodiment, the weighted probabilities of the drug product records 300 may decrease and increase in a zero-sum method. Thus, the overall weighted probability of the drug product records 300 may remain the same or at a similar amount in response to a reduction 810 or an increase 812. For example, the weighted probability of the first drug product record 300 may decrease by 15% and the weighted probability of the second drug product record 300 may increase by 15%. In one embodiment, determining whether an increase and decrease in one or more drug product records 300 is equal or similar may include determining based on user input, a drug product value 350, the frequency of occurrence of a drug product value 350 in the population of drug product records 402, or the like. For example, half of the population of drug product records 402 may include the drug product value 354 "Percocet" for the drug product feature 314 of "Drug Name." Reducing the weighted probability of "Percocet" may include reducing a weighted probability by 1% and increasing the weighted probability of drug product records 300 without the value 354 "Percocet" may include increasing a weighted probability by 7%. A user of ordinary skill in the art may recognize other ways to implement a decrease and increase of one or more drug product criteria in an equal or zero-sum manner.

In one embodiment, reducing 810 the weighted probability of the first drug product record or increasing 812 the weighted probability of the second drug product record may be based on differing drug product values 350 of the same drug product feature 310. For example, the first set of drug product criteria 404 may include the drug product feature 318 "Location." In some embodiments, reducing 810 the weighted probability of the first drug product record or increasing 812 the weighted probability of the second drug product record may be based on different drug product features 310. For example, the first set of drug product criteria 404 may include the drug product feature 318 for "Location," and reducing 810 the weighted probability of a first drug product record may include reducing the weighted probability of the drug product records 300 whose drug product value 358 include "Montana," "New York," or "Georgia." A second set of drug product criteria may include the drug product feature 314 of "Drug Name," and increasing 812 the weighted probability of the second drug product record may include increasing the weighted probability of the drug product records 300 that include the drug product value 354 of "Percocet."

In one embodiment, the weighted probability of a drug product record 300 may include a base weighted probability. The base weighted probability may include an initial weighted probability that has not increased or decreased in response to iterations of the method 800. In response to reducing or increasing the weighted probability of a drug product record 300, the weighted probability of the drug product record 300 may move away from the base weighted probability. In one embodiment, in response to reducing 810 or increasing 812 the weighted probability of one or more drug records 300, the weighted probability of a drug product record 300 may settle around a certain value. This value may have been unknown prior to a drug audit, but over time, the weighted probability may approach this value. Furthermore, in one embodiment, the weighted probability of a first drug product record 300 may fluctuate for a short time based on the randomized selections of recent drug audits, and the weighted probability of a second drug product record 300 may automatically respond to this fluctuation. This may lead to a more fair, flexible, and unbiased selection process for drug audits.

In some embodiments, the present disclosure improves the functionality of a computing device. For example, in one embodiment, the systems and methods described herein may facilitate the automated creation of a subset of drug product records for a drug audit. The systems and methods may improve the way a computing device, such as the auditor 108, stores and retrieves data. For example, by receiving the population of drug product records 402 from a distributed ledger, the population of drug product records 402 can be more secure, more accessible, more tamper-resistant, or more traceable than a population of drug product records stored, for example, in a file system, centralized database, or other storage means. Furthermore, the population of drug product records 402 may include data that is updated in or near real-time that may be due to the distributed nature of the ledger. The systems and methods may enhance the operation of the auditor 108 by using programmable operational characteristics, such as customizable drug product criteria, without a tradeoff in fair random sampling. This may result because the criteria may allow the auditor 108 to tailor the random sampling while simultaneously reducing bias introduced by a human user operating the auditor 108.

As discussed herein, the present disclosure includes components that are not well-understood, routine, or conventional. For example, applying a weighted probability to one or more drug product records 300 of a population of drug product record 402 and randomly selecting a first subset of drug product record 406 based on those weighted probabilities is not conventional. This unconventional activity may result in a randomized selection of drug products for audit that is more fair and better representative of the population of drug products than a purely random sampling or other types of random sampling.

Aspects of the present invention are described herein with reference to flowchart illustrations or block diagrams of methods, apparatuses, systems, and computer program products. It will be understood that a block, combinations of blocks, or a part of a block of a flowchart illustration or block diagram can be implemented by computer readable program instructions, by computer hardware, or a combination of both. The schematic flowchart diagrams or schematic block diagrams in the Figures illustrate the architecture, functionality, and operation of possible implementations of apparatuses, systems, methods, and computer program products.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. The computer readable program instructions may comprise one or more physical or logical blocks of computer instructions which may, for instance, be organized as an object, procedure, or function. Nevertheless, theses computer readable program instructions need not be physically located together, but may comprise disparate instructions stored in different locations which, when joined logically together, comprise the functionality or segment of the functionality of a block and achieve the stated purpose of the block. These computer readable program instructions may also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart or block diagram block or blocks.

As mentioned above, a block, combinations of blocks, or a part of a block of a flowchart illustration or block diagram may be implemented as computer hardware. The computer hardware may include a hardware circuit comprising custom very-large-scale integration (VLSI) circuits or gate arrays, off-the-shelf semiconductors such as logic chips, transistors, or other discrete components. A block, combination of blocks, or part of a block may also be implemented in programmable hardware devices such as field programmable gate arrays, programmable array logic, programmable logic devices or the like.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams or flowchart diagrams, and combinations of blocks in the block diagrams or flowchart diagrams, can be implemented by special purpose hardware-based systems that perform the specified functions or acts, or combinations of special purpose hardware and program code.

While the making and using of various embodiments of the present invention are discussed in detail herein, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

Numerous other objects, advantages and features of the present disclosure will be readily apparent to those of skill in the art upon a review of the drawings and description of the embodiments.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions or methods disclosed and claimed herein may be made or executed without undue experimentation in light of the present disclosure. While the compositions and methods of this invention have been described in terms of the embodiments included herein, it will be apparent to those of ordinary skill in the art that variations may be applied to the compositions or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful drug selection for audit method, it is not intended that such references be construed as limitations upon the scope of this invention except as set forth in the following claims.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed:

1. A computer-implemented method of auditing drug supply chain data gathered from a distributed ledger, comprising:
   receiving a population of drug product records from the distributed ledger;
   receiving a first set of drug product criteria;
   determining a weighted probability for one or more drug product records of the population of drug product records based one the first set of drug product criteria; and
   generating a randomized first subset of drug product records from the population of drug product records based on the weighted probability of the one or more drug product records.

2. The computer-implemented method of claim 1, wherein the population of drug product records comprises a plurality of drug product records corresponding to auditable drug products.

3. The computer-implemented method of claim 1, wherein a drug product record of the population of drug product records comprises:
   one or more drug product features; and
   one or more drug product values.

4. The computer-implemented method of claim 3, wherein a drug product feature comprises at least one of:
   a product identification number;
   a drug name;
   an expiration date;
   a location; or
   a drug schedule classification.

5. The computer-implemented method of claim 1, wherein receiving the population of drug product records from the distributed ledger comprises:
   receiving, at an auditor computing device, one or more drug product records from the distributed ledger; and
   assembling the population of drug product records from the received one or more drug product records.

6. The computer-implemented method of claim 1, wherein the first set of drug product criteria comprises at least one of:
   a drug product feature;
   a drug product value; or
   an instruction.

7. The computer-implemented method of claim 1, wherein receiving the first set of drug product criteria comprises receiving the first set of drug product criteria from at least one of:
   user input;
   a file; or
   a remote computing device.
8. The computer-implemented method of claim 1, wherein:
   a drug product record of the population of drug product records comprises a location drug product feature and a corresponding location drug product value;
   the first set of drug product criteria comprises
      a location drug product feature, and
      an instruction to adjust the weighted probability of the drug product record of the population of drug product records in response to the location drug product value of the drug product record; and
   determining the weighted probability for one or more drug product records of the population of drug product records based on the first set of drug product criteria comprises increasing the weighted probability of the drug product record of the population of drug product records based on the drug product record including the location drug product value.
9. The computer-implemented method of claim 1, wherein:
   a drug product record of the population of drug product records comprises a drug name drug product feature and a corresponding drug name drug product value;
   the first set of drug product criteria comprises
      a drug name drug product feature, and
      an instruction to adjust the weighted probability of the drug product record of the population of drug product records in response to the drug product value of the drug product record; and
   determining the weighted probability for one or more drug product records of the population of drug product records based on the first set of drug product criteria comprises increasing the weighted probability of the drug product record of the population of drug product records based on the drug product record including the drug name drug product value.
10. The computer-implemented method of claim 1, wherein generating the randomized first subset of drug product records from the population of drug product records based on the weighted probability of the one or more drug product records comprises randomly selecting at least one drug product record from the population of drug product records, wherein a probability of the at least one drug product record is based on the weighted probability of the at least one drug product record.
11. The computer-implemented method of claim 1, further comprising:
   receiving a second set of drug product criteria from user input; and
   selecting a second subset of drug product records from the first subset of drug product records based on the second set of drug product criteria,
   wherein generating the randomized first subset of drug product records from the population of drug products records comprises generating the randomized first subset of drug product records from the second subset of drug product records.
12. The computer-implemented method of claim 1, further comprising removing a second subset of drug product records from the population of drug product records.
13. A computer-implemented method of auditing drug supply chain data gathered from a distributed ledger, comprising:
   receiving a population of drug product records from the distributed ledger;
   receiving a first set of drug product criteria;
   determining a first weighted probability for one or more drug product records of the population of drug product records based on the first set of drug product criteria;
   generating a randomized first subset of drug product records from the population of drug product records based on the first weighted probability of the one or more drug product records; and
   removing a second subset of drug product records from the population of drug product records.
14. The computer-implemented method of claim 13, wherein removing the second subset of drug product records from the population of drug product records comprises removing the second set of drug product records based on at least one of:
   the first set of drug product criteria; or
   the first subset of drug product records.
15. The computer-implemented method of claim 13, further comprising:
   determining a second weighted probability for one or more drug product records of the population of drug product records based on the first set of drug product criteria, wherein the population of drug product records does not include the second subset of drug product records; and
   generating a randomized third subset of drug product records from the population of drug product records based on the second weighted probability.
16. The computer-implemented method of claim 13, further comprising:
   receiving a time period from user input; and
   reinserting the second subset of drug product records into the population in response to the time period expiring.
17. The computer-implemented method of claim 16, wherein:
   receiving the time period from user input comprises receiving a plurality of time periods; and
   each of the plurality of time periods include an equal length of time.
18. A computer-implemented method of auditing drug supply chain data gathered from a distributed ledger, comprising:
   receiving a population of drug product records from the distributed ledger;
   receiving a first set of drug product criteria;
   determining a weighted probability for one or more drug product records of the population of drug product records based on the first set of drug product criteria;
   generating a randomized first subset of drug product records from the population of drug product records based on the weighted probability of the one or more drug product records;
   reducing a weighted probability of a first drug product record based on the first subset of drug product records; and
   increasing a weighted probability of a second drug product record based on the first subset of drug product records.
19. The computer-implemented method of claim 18, wherein reducing the weighted probability of the first drug product record includes reducing the weighted probability by a fairness factor divided by the number of drug product records in the first subset of drug product records.

20. The computer-implemented method of claim 18:
wherein increasing the weighted probability of the second drug product record includes reducing the weighted probability according to the equation $$P'_u = P_u + \sum_i^{N-X} \frac{Pi - P'i}{n - x};$$

and
wherein u is the second drug product record, $P'_u$ is the increased weighted probability of the second drug product record, $P_u$ is the unincreased weighted probability of the second drug product record, N is the population of drug product records, X is the first subset of drug product records, $P_i$ is the weighted probability of a drug product record i of the first subset of drug product records, $P'_i$ is an increased weighted probability of the drug product record i of the first subset of drug product records, n is the number of drug product records in the population of drug product record, and x is the number of drug product records in the first subset of drug product records.

* * * * *